United States Patent [19]

Niznick

[11] Patent Number: 5,071,350
[45] Date of Patent: Dec. 10, 1991

[54] TILTABLE, ADJUSTABLE, INSERT FOR A DENTAL IMPLANT

[75] Inventor: Gerald A. Niznick, Encino, Calif.

[73] Assignee: Core-Vent Corporation, Encino, Calif.

[21] Appl. No.: 497,084

[22] Filed: Mar. 21, 1990

[51] Int. Cl.⁵ .............................................. A61C 8/00
[52] U.S. Cl. .................................. 433/173; 433/174; 433/201.1
[58] Field of Search ............... 433/169, 173, 174, 175, 433/176, 201.1

[56] References Cited

U.S. PATENT DOCUMENTS

| | | | |
|---|---|---|---|
| 4,758,161 | 7/1988 | Niznick | 433/173 |
| 4,793,808 | 12/1988 | Kirsch | 433/173 |
| 4,832,601 | 5/1989 | Linden | 433/173 |
| 4,907,969 | 3/1990 | Ward | 433/173 |

Primary Examiner—John J. Wilson

[57] ABSTRACT

A tiltable, rotatable, adjustable, castable insert adapted for use with dental implants includes two parts: first, a shaft with a receptacle attached to the shaft; second, within the receptacle, a tiltable, rotatable, adjustable prosthesis connector.

19 Claims, 2 Drawing Sheets

TILTABLE, ADJUSTABLE, INSERT FOR A DENTAL IMPLANT

This invention relates to a tiltable, adjustable, rotatable, castable insert adapted for use with a dental implant, particularly with an endosseous dental implant that has a threaded, internal passage for engaging the insert.

The invention relates to an insert adapted for use with a dental implant, particularly with a dental implant having a threaded, internal passage for engaging the insert, comprising a first or base part including shaft means having a threaded or unthreaded exterior wall adapted for engaging a threaded or unthreaded passage inside a dental implant, particularly an endosseous dental implant such as the Core-Vent ® dental implant, the Screw-Vent ® dental implant, the Swede-Vent ® dental implant, and the Micro-Vent ® dental implant.

Atop, and connected to the threaded shaft means are receptacle means adapted to support a second part, namely a tiltable, rotatable prosthesis connector means. The first part and the second part are of a size and shape appropriate for forming the two parts together, by casting, to form an insert with a prosthesis-engaging portion tilted to a desired angle with reference to the shaft means.

The receptacle means includes cup means and removable means for positioning the prosthesis connector means in the receptacle means. This removable means is preferably a plastic, heat-removable body within the cup means. The prosthesis connector means preferably includes a tiltable, rotatable, rounded member embedded in the plastic material; flange means atop this rounded member; and a prosthesis-engaging projection above the flange member.

In preferred embodiments, the receptacle means comprises the cup means connected to the shaft means. The cup means includes a base member joined to a cylindrically-shaped wall member. The wall member has an angled, circumferential opening at the top.

Within the receptacle means, and preferably filling the receptacle, is a plug of plastic material, preferably of wax or a thermoplastic or other heat-removable plastic.

In preferred embodiments, the tiltable, rotatable prosthesis connector means includes a rounded, preferably ball-shaped member embedded in the removable means, e.g., the wax body. Connected to this rounded member, and projecting above the removable means, are flange means, preferably with a round profile and flat upper and lower surfaces. Atop the flange means are prosthesis-connecting means, preferably in the form of a projection from the top of the flange member. In preferred embodiments, the projection is frustoconical in shape, with the larger base of the frustoconical member attached to the flange, and the smaller, preferably flat base at the top of the prosthesis connector.

In preferred embodiments, the prosthesis connector includes means for joining the prosthesis connector to a dental prosthesis. For example, the projection can include an internally-threaded shaft projecting downwardly from its upper surface, or may include threads along at least a portion of its exterior wall for engaging such a connector, or both.

In preferred embodiments, the insert is made of a metal such as titanium or titanium alloy (6-aluminum/4 vanadium). In some embodiments, the receptacle means can be made from titanium, and the prosthesis connector means, from a titanium alloy, or vice-versa.

In use, the insert is inserted into a threaded or unthreaded passage in a dental implant that has been placed in a patient's jaw. The user then makes an impression of the patient's jaw, including the dental implant, and transfers an implant analog with the impression to a stone working model using a transfer head attached to the implant for this procedure. The user then removes the transfer head from the analog, and inserts the first or base part of the insert. The removable member with the tiltable, rotatable second part attached are inserted into the receptacle of the first or base part. The tiltable, rotatable member is moved to a desired angle, and fixed in place using wax or other removable positioning means. Thereafter, the three interconnected parts are removed from the analog of the implant, and a spine is attached at the midsection of the removable material. The user then invests the component and casts, using gold or acceptable dental alloy, to unite the first and second parts to one another to form a custom angled insert.

BRIEF DESCRIPTION OF THE DRAWINGS

The dental insert of this invention can better be understood by reference to the drawings in which.

DESCRIPTION OF THE PREFERRED EMBODIMENTS

Figure 1:
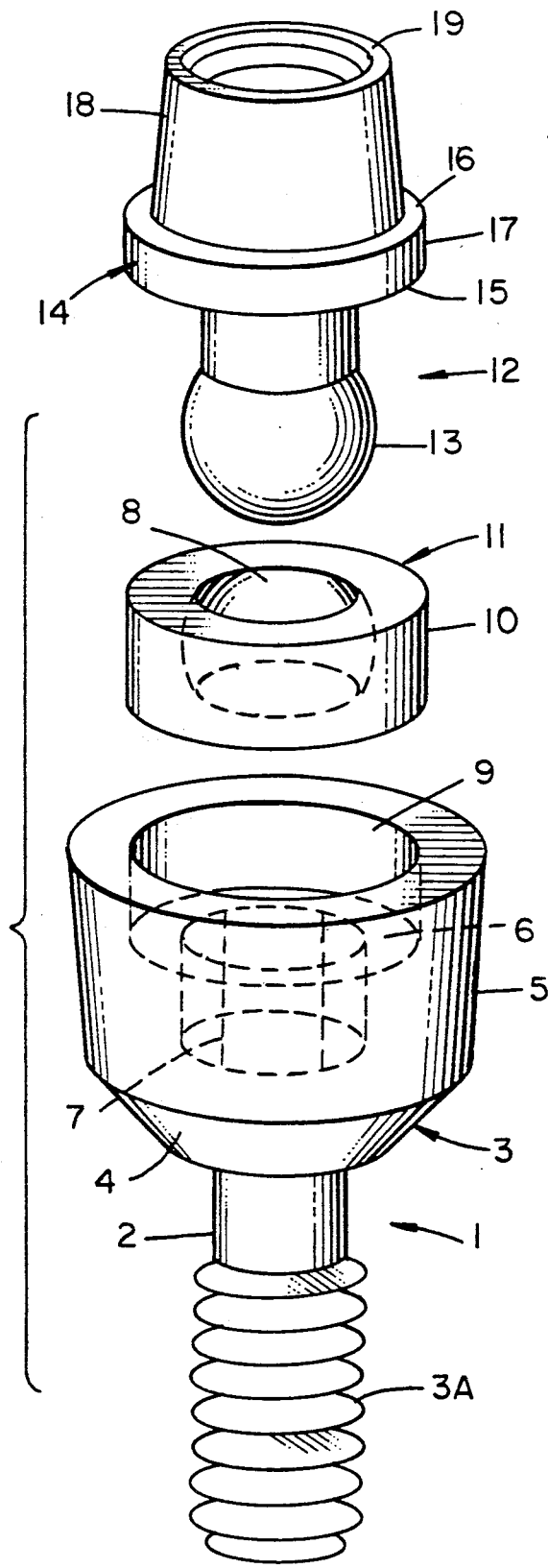
FIG. 1 is a perspective view of a preferred embodiment of the new dental insert with the parts separated for clarity.
Figure 2:
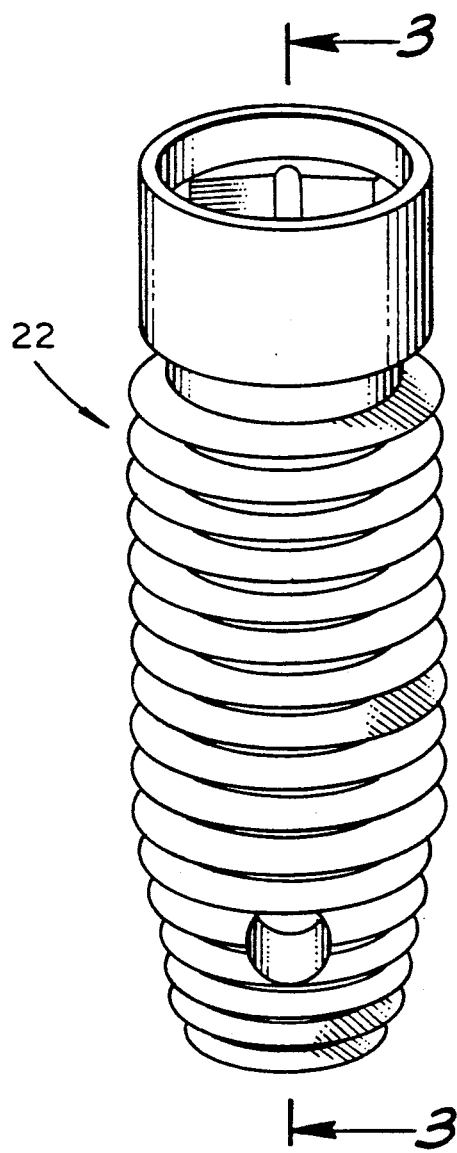
FIGS. 2 and 3 show a perspective view and a cross-sectional view, in elevation, taken on line 3—3 of FIG. 3, showing the construction of a dental implant adapted for receiving the insert embodiment shown in FIG. 1.
Figure 3:
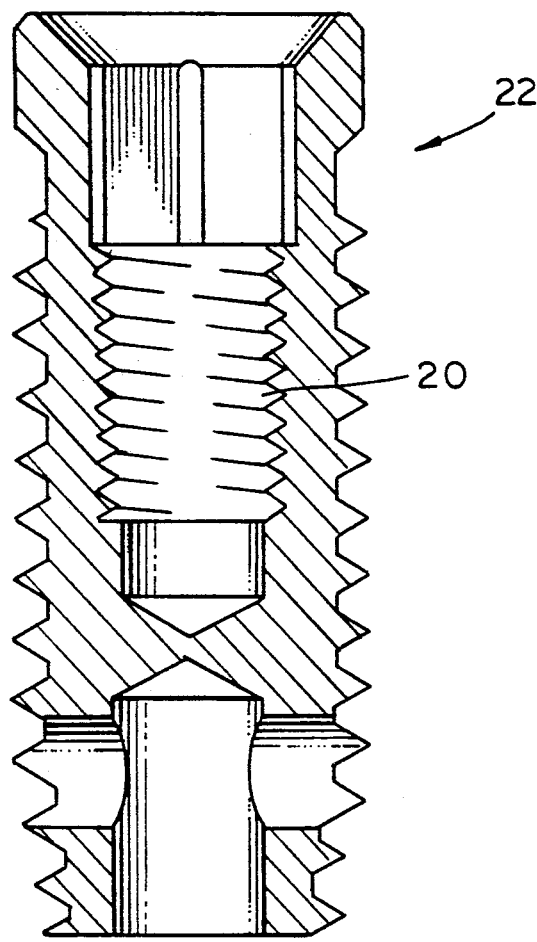
Figure 4:
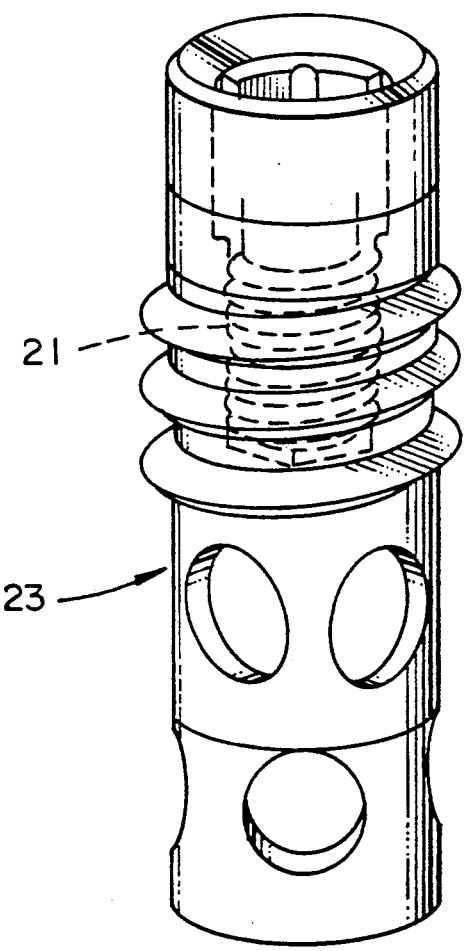
FIG. 4 shows a perspective view of another dental implant adapted to receive the preferred insert embodiment of this invention shown in FIG. 1.

FIGS. 1 shows a preferred embodiment of the new insert 1. Insert 1 includes shaft 2 with exterior threaded wall portion 3A on shaft 2. Joined to shaft 2 is receptacle 3 having base member 4 and circumferential side wall member 5 connected to base member 4. Within receptacle 3, on inner surface 6 of base member 4, is opening 7. Opening 7 is adapted to receive a tool such as an Allen wrench for engaging the insert and for placing the insert into threaded shafts 20 and 21 of dental implants 22 and 23 such as seen in FIGS. 2-4.

Within receptacle 3 is thermoplastic plug 11. Sidewall 10 of plug 11 is of a size and shape to fit snugly within opening 9. Embedded within plug 11 is prosthesis connector means 12. Connector means 12 includes ball-shaped member 13 embedded within complementary-shaped opening 8 in plastic material 11. Atop ball-shaped member 13 is flange member 14 that has flat lower surface 15, flat upper surface 16 and circular periphery surface 17. Attached to upper surface 16 of flange member 12 is frustoconical projection 18. Frustoconical projection 18 has its smaller base 19 at the top of projection 18.

. Connector part 12 is tiltable and rotatable over an angular path of approximately 40° from the longitudinal axis of shaft member 2. This tilting/rotating freedom of movement permits alignment of connector 12 at a desired angle with insert 1 engaged in the internal, threaded shaft of a dental implant.

In use, the user adjusts connector 12 to a desired angle with the insert in place in a dental implant, removes the insert from the dental implant, and then casts the insert in a castable metal such as gold or gold alloy, removing plastic material 11 from receptable 3 and fixing connector 12 in the cast metal. Thereupon, the insert can again be placed in the internal shaft of the dental implant, and a suitable prosthesis joined to it.

What is claimed is:

1. A tiltable, adjustable, rotatable, castable insert adapted for use with a dental implant includes shaft means having an exterior wall adapted for engaging a passage inside a dental implant; atop said shaft means, and connected to said shaft means, receptacle means and, within said receptacle means, a heat-removable body for supporting a tiltable, rotatable prosthesis connector means; and, atop said support means, tiltable, rotatable prosthesis connector means, said prosthesis connector means being adapted for positioning in said heat-removable body and for casting at a desired angle with reference to said support means.

2. The connector means of claim 1 wherein said receptacle means comprises cup means with said heat-removable body within said cup means.

3. The insert of claim 2 wherein said prosthesis connector means includes a tiltable, rotatable, rounded member embedded in said body; flange means atop said rounded member; and a prosthesis-engaging projection connected to and above said flange member.

4. The insert of claim 3 wherein the exterior wall of said shaft means is threaded.

5. The insert of claim 3 wherein the exterior wall of said shaft means is unthreaded.

6. The insert of claim 2 wherein the exterior wall of said shaft means is threaded.

7. The insert of claim 2 wherein the exterior wall of said shaft means is unthreaded.

8. The insert of claim 1 wherein the exterior wall of said shaft means is threaded.

9. The insert of claim 1 wherein the exterior wall of said shaft means is unthreaded.

10. A tiltable, rotatable, adjustable, castable insert adapted for use with an endosseous dental implant that has a threaded, internal passage for engaging the insert comprising shaft means having a threaded exterior wall adapted for engaging the threaded exterior wall adapted for engaging the threaded passage inside said implant; atop said shaft means, and connected to said shaft means, receptacle means and, within said receptacle means, a heat-removable body for supporting tiltable, rotatable prosthesis connector means; and, within said receptacle means, tiltable, rotatable prosthesis connector means.

11. The connector means of claim 10 wherein said receptacle means includes cup means and said heat-removable body is plastic and is within said cup means.

12. The insert of claim 11 wherein said prosthesis connector means includes a tiltable, rotatable, rounded member embedded in said body; flange means atop said rounded member; and a prosthesis-engaging projection connected to and above said flange member.

13. The insert of claim 11 wherein the exterior wall of said shaft means is threaded.

14. The insert of claim 11 wherein the exterior wall of said shaft means is unthreaded.

15. The insert of claim 10 wherein the exterior wall of said shaft means is threaded.

16. The insert of claim 10 wherein the exterior wall of said shaft means is unthreaded.

17. A tiltable, adjustable, castable insert adapted for use with an endosseous dental implant comprising shaft means having an exterior wall adapted for engaging a passage within said implant; connected to said shaft means, a receptacle means adapted to support a tiltable, rotatable prosthesis connector means; and, within said receptacle means, a heat-removable body with a tiltable, rotatable prosthesis connector means embedded in, and free to tilt and rotate in said body.

18. The insert of claim 17 wherein the exterior wall of said shaft means is threaded.

19. The insert of claim 17 wherein the exterior wall of said shaft means is unthreaded.

* * * * *